United States Patent [19]

Skelnik et al.

[11] Patent Number: 5,102,653

[45] Date of Patent: Apr. 7, 1992

[54] NON-PRIMATE VITREAL REPLACEMENT MODEL

[76] Inventors: Debra L. Skelnik, P.O. Box 758, Rte. 3, Cambridge, Minn. 55008; Richard L. Lindstrom, 20050 Lakeview Ave., Excelsior, Minn. 55331

[21] Appl. No.: 463,485

[22] Filed: Jan. 11, 1990

[51] Int. Cl.$^5$ ............................................. A61K 49/00
[52] U.S. Cl. ...................................... 424/9; 514/912; 514/54
[58] Field of Search ............................ 424/9; 514/912

[56] References Cited

U.S. PATENT DOCUMENTS 4,716,154 12/1987 Mälson et al. ..................... 514/54
4,819,617 4/1989 Goldberg et al. .................. 514/912

OTHER PUBLICATIONS

"Replacement of the Vitreous Body in the Monkey by Reconstituted Vitreous and by Hyaluronic Acid", by Balax and Sweeney, Modern Problems in Ophthalmology, vol. 4, pp. 230-232.

"The Injection of Hyaluronic Acid and Reconstituted Vitreous into the Vitreous Cavity", by Balazs and Sweeney, New and Controversial Aspects of Retinal Detachment, pp. 371-376.

"Studies on the Structure of the Vitreous Body. VIII. Comparative Biochemistry", by Balazs, Laurent, Laurent, DeRoche and Bunney, Archives of Biochemistry and Biophysics, 81, 464-479.

Primary Examiner—Frederick E. Waddell
Assistant Examiner—Zohreh A. Fay
Attorney, Agent, or Firm—Hugh D. Jaeger

[57] ABSTRACT

This is a non-primate vitreal replacement process that quantitates the inflammatory response to viscoelastic agents or solutions. More specifically, the rabbit vitreal replacement process consists of the surgical replacement of a small volume of the central gel vitreous of the rabbit with a viscoelastic agent or solution, and measuring the invasion of white blood cells in the vitreous and anterior chamber at 48 hours post injection. Additional parameters measured are anterior chamber flare, haze and flare in the vitreal chamber, ocular fundus clarity, presence of iris congestion, lens involvement, corneal clarity, conjunctival congestion and conjunctival swelling. In this process, the rabbit is evaluated prior to injection of the viscoelastic agent or solution and 48 hours post injection. Each parameter is evaluated on a scale of 0 to 5. A non-inflammatory sample consists of a mean total score of equal to or less than one or a vitreal cell count less than 50 cells/mm$^3$. This is an extremely sensitive system for detecting small amounts of inflammatory agents in viscoelastic agents or solutions. The test solution is rated as acceptable for veterinary or human use if a non-inflammatory response is obtained in this process.

24 Claims, 8 Drawing Sheets

| Clinical Grade | Aqueous Flare | Anterior Chamber Cells/mm3 | Vitreous Cells/mm3 | Vitreous Haze Ocular Fundus | Keratic Precipitates |
|---|---|---|---|---|---|
| 0 | Barely detectable | 0 | 0 | No Haze Fundus Clear | None |
| 1 | Slight | <50 Slight | <50 Slight | No Haze Fundus Clear | None |
| 2 | Moderate | 51-200 Moderate | 51-200 Moderate | Slight Haze Fundus Clear | Just Detectable |
| 3 | Moderate-Severe | 201-600 Moderate-Severe | 201-600 Moderate-Severe | Marked haze Fundus details Visable | Small |
| 4 | Severe | 601-1200 Severe | 601-1200 Severe | Severe haze Red fundus reflex No fundus details visable | Medium |
| 5 | Very Severe | >1200 Very Severe | >1200 Very Severe | Severe haze Gray fundus reflex | Large |

FIG. 1A

| Clinical Grade | Conjunctival Congestion | Conjunctival Swelling | Conjunctival Discharge |
|---|---|---|---|
| 0 | None<br>Blanched to reddish pink without perilimbal injection (except at 12:00 and 6:00 o'clock positions) | Normal, no swelling | Normal. No Discharge. |
| 1 | Slight, flushed reddish color confined to the palpebral conjunctiva with some perilimbal injection | Slight swelling<br>No eversion of lids | Slight discharge |
| 2 | Moderate, flushed, reddish color confined to the palpebral conjunctiva with some perilimbal injection | Moderate swelling<br>No eversion of lids | Slight to moderate discharge |
| 3 | Bright red color of the palpebral conjunctiva with perilimbal injection | Moderate swelling<br>Misalignment of lids | Moderate-Severe discharge |
| 4 | Dark, beefy red color with congestion of both the bulbar and the paplebral conjunctiva. | Moderate swelling with partial eversion of lids | Severe discharge |
| 5 | Dark, beefy red color with congestion of both the bulbar and the paplebral conjunctiva, pronounced perilimbal injection and petechia on the conjunctiva | Severe swelling<br>Eversion of upper and lower lids | Very Severe Discharge |

FIG. 1B

| Clinical Grade | Iris Congestion | Corneal Clarity | Lens Involvement |
|---|---|---|---|
| 0 | Normal iris with out any hyperemia. | Normal cornea. | No lens involvement |
| 1 | Minimal injection of secondary vessels but not tertiary. | Minimal loss of transparency. | Slight lens opacity |
| 2 | Moderate injection of the secondary and tertiary vessels. | Moderate loss of transparency. Cloudiness extends to endothelium. | Moderate lens opacity Minimal suture line visible |
| 3 | Moderate injection of the secondary and tertiary vessels. Slight swelling of iris stroma. | Moderate to severe loss of transparency. Involvement of the entire thickness of the cornea. Detail visable. | Moderate to severe lens opacity Moderate suture line visible |
| 4 | Severe injection of he secondary and tertiary vessels, marked swelling of the iris stroma. | Severe loss of transparency. Involvement of the entire thickness of the cornea. Detail visable | Severe lens opacity Severe suture line visable |
| 5 | Severe injection of he secondary and tertiary vessels, marked swelling of the iris stroma. Iris is rugose, hyphema in the anterior chamber. | Severe loss of transparency. Involvement of the entire thickness of the cornea. No detail visable. | Total lens opacity |

FIG. 1C

| Clinical Grade | Aqueous Flare | Anterior Chamber Cells/mm3 | Vitreous Cells/mm3 | Vitreous Haze Ocular Fundus | Keratic Precipitates |
|---|---|---|---|---|---|
| 0 | Barely detectable | 0 | 0 | No Haze Fundus Clear | None |
| 1 | Slight | <50 Slight | <50 Slight | No Haze Fundus Clear | None |

FIG. 2A

| Clinical Grade | Conjunctival Congestion | Conjunctival Swelling | Conjunctival Discharge |
|---|---|---|---|
| 0 | None<br>Blanched to reddish pink without perilimbal injection (except at 12:00 and 6:00 o'clock positions) | Normal, no swelling | Normal. No Discharge. |
| 1 | Slight, flushed reddish color confined to the palpebral conjunctiva with some perilimbal injection | Slight swelling<br>No eversion of lids | Slight discharge |

FIG. 2B

| Clinical Grade | Iris Conjestion | Corneal Clarity | Lens Involvement |
|---|---|---|---|
| 0 | Normal iris with out any hyperemia. | Normal cornea. | No lens involement |
| 1 | Minimal injection of secondary vessels but not tertiary. | Minimal loss of transparency. | Slight lens opacity |

FIG. 2C

|  | Rhesus Monkey | | New Zealand White Rabbits | |
|---|---|---|---|---|
|  | Pre Injection | 48 Hours Post Injection | Pre Injection | 48 Hours Post Injection |
| Aqueous Flare | 0 ± 0 | .5 ± .5 | 0 ± 0 | 1 ± 0 |
| Anterior Chamber Cells/mm3 | 0 ± 0 | 1 ± 0<br>15 ± 4 cells/mm3 | 0 ± 0 | 1 ± 0<br>11 ± 4 cells/mm3 |
| Vitreal Chamber Cells/mm3 | 1 ± 0<br>2 ± 2 cells/mm3 | 2 ± 0<br>21 ± 10 cells/mm3 | 1 ± 0<br>7 ± 2 cells/mm3 | 2 ± 0<br>45 ± 8 cells /mm3 |
| Vitreal Haze | 0 ± 0 | 0 ± 0 | 0 ± 0 | 0 ± 0 |
| Ocular Fundus | 0 ± 0 | 0 ± 0 | 0 ± 0 | 0 ± 0 |
| Keratic Precipitates | 0 ± 0 | 0 ± 0 | 0 ± 0 | 0 ± 0 |
| Conjunctival Conjestion | 0 ± 0 | 1 ± 0 | 0 ± 0 | 2 ± 0 |
| Conjunctival Swelling | 0 ± 0 | 1 ± 0 | 0 ± 0 | 1 ± 0 |
| Conjunctival Discharge | 0 ± 0 | 0 ± 0 | 0 ± 0 | 0 ± 0 |
| Iris Conjestion | 0 ± 0 | 1 ± 1 | 0 ± 0 | 2 ± 1 |
| Corneal Clarity | 0 ± 0 | 0 ± 0 | 0 ± 0 | 0 ± 0 |
| Lens Involvement | 0 ± 0 | 0 ± 0 | 0 ± 0 | 0 ± 0 |
| Mean Total Score |  | 0.54<br>Non-Inflammatory |  | 0.75<br>Non-Inflammatory |

FIG. 3

|  | New Zealand White Rabbit*<br>Zymozan A 1 mg/ml | | New Zealand White Rabbits**<br>Ocugel™ | |
|---|---|---|---|---|
|  | Pre Injection | 48 Hours<br>Post Injection | Pre Injection | 48 Hours<br>Post Injection |
| Aqueous Flare | 0 ± 0 | 2 ± 1 | 0 ± 0 | 0 ± 0 |
| Anterior Chamber<br>Cells/mm3 | 0 ± 0 | 2 ± 0<br>89 ± 35 cells/mm3 | 0 ± 0 | 1 ± 0<br>5 ± 2 cells/mm3 |
| Vitreal Chamber<br>Cells/mm3 | 0 ± 0 | 3 ± 0<br>466 ± 114 cells/mm3 | 0 ± 0 | 1 ± 0<br>10 ± 5 cells/mm3 |
| Vitreal Haze | 0 ± 0 | 3 ± 0 | 0 ± 0 | 0 ± 0 |
| Ocular Fundus | 0 ± 0 | 1 ± 0 | 0 ± 0 | 0 ± 0 |
| Keratic Precipitates | 0 ± 0 | 0 ± 0 | 0 ± 0 | 0 ± 0 |
| Conjunctival Congestion | 0 ± 0 | 3 ± 0 | 0 ± 0 | 0 ± 0 |
| Conjunctival Swelling | 0 ± 0 | 2 ± 0 | 0 ± 0 | 0 ± 0 |
| Conjunctival Discharge | 0 ± 0 | 1 ± 1 | 0 ± 0 | 0 ± 0 |
| Iris Congestion | 0 ± 0 | 2 ± 0 | 0 ± 0 | 0 ± 0 |
| Corneal Clarity | 0 ± 0 | 1 ± 1 | 0 ± 0 | 0 ± 0 |
| Lens Involvement | 0 ± 0 | 0 ± 0 | 0 ± 0 | 0 ± 0 |
| Mean Total Score |  | 1.66<br>Inflammatory |  | 0.16<br>Non-Inflammatory |

* 3 Reps
** 21 Reps

FIG. 4

NON-PRIMATE VITREAL REPLACEMENT MODEL

BACKGROUND OF THE PRESENT INVENTION

1. Field of the Invention

The present invention pertains to a non-primate vitreal replacement process that quantitates the inflammatory response to viscoelastic agents or solutions.

2. Description of the Prior Art

The owl monkey (Aotus trivigatus) was used as a process for measuring the inflammatory response of intravitreous hyaluronic acid injections. The owl monkey was selected because it was found that when full grown, this new world monkey had a liquid vitreous. [Balazs, Laurent, DeRoche and Bunney, (1959) Studies on the structure of the vitreous body VIII. Comparative Biochemistry. Arch. Biochem Biophys. 81, 464–79.] The presence of a liquid rather than a gel vitreous was a prerequisite for these tests. The exchange of viscous liquid vitreous with a biopolymer solution had to be achieved with minimal surgical trauma in order to evaluate the tolerance of the vitreous substance used. The owl monkey vitreous test was consequently developed as an extremely sensitive method to evaluate the inflammatory reaction in the vitreous after the injection of viscoelastic solutions. [Balazs, E.A. and Sweeney, D.B. (1966) Replacement of the vitreous body of monkeys with reconstituted vitreous and hyaluronic acid. In Modern Problems in Ophthalmology (Surgery of retinal vascular diseases and prophylactic treatment of retinal detachment, Amersfoort 1963 (ed. Streiff, E.B.). Vol 4 pp. 230–32.] [S. Karger, Basel, New York. Balazs, E.A. and Sweeney, D. (1966). The injection of hyaluronic acid and reconstituted vitreous into the vitreous cavity. In New and Controversial Aspects of Retinal Detachment (Ed. McPherson) pp. 371-6. Harper and Row, New York.] The liquid vitreous of the owl monkey can be easily replaced without mechanical damage to the retina and lens. The minimal operational trauma permits a very accurate and sensitive evaluation of the the tolerance of the vitreal implant.

These studies were aimed at establishing whether or not a highly purified special fraction of sodium hyaluronate when implanted into the vitreous, causes any immediate inflammatory reaction in the eye. U.S. Pat. No. 4,141,973 to Balazs describes a modified owl monkey test to test the inflammatory reaction of ultrapure hyaluronic acid.

Another primate that has been used to test the inflammatory reaction of ultrapure hyaluronic acid is the rhesus monkey. Although the total volume of the vitreous of the adult rhesus eye is approximately 24% larger than the owl monkey eye, the volume of the liquid vitreous is smaller (0.8 to 1.2 ml) in the rhesus than the owl monkey eye (1.8–2.2 ml). In the rhesus monkey, only 0.5 ml of vitreous can be removed and replaced. By reducing the volume of vitreous removed and replaced, the incidence of eyeball collapse is greatly reduced, and therefore, there is less traumatic injury to the blood aqueous barrier. The rhesus monkey has been shown to have similar inflammatory reactions as the owl monkey, after vitreal injection of Healon ®. The rhesus monkey can also be used as an extremely sensitive system for detecting small amounts of inflammatory agents. (Denlinger, J.L. and Balazs, E.A., Replacement of the Liquid Vitreous with Sodium Hyaluronate in Monkeys. Experimental Eye Research (1980) 31, 81–99.)

The present invention overcomes the disadvantages of the prior art by providing a process for quantifying the inflammatory response to viscoelastic agents or solutions in New Zealand White rabbit, which is readily available.

SUMMARY OF THE INVENTION

This invention pertains to the use of a non-primate vitreal replacement process to distinguish between inflammatory and non-inflammatory viscoelastic agents and solutions for use in veterinary and human applications. The viscoelastic agents or solutions are commonly used in ocular and surgical applications, and are used during surgery to protect cells from mechanical trauma, to maintain or create tissue spaces, to ensure separation and lubrication of tissue surfaces, to permit the manipulation of tissues without mechanical damage. Impurties present in sterile viscoelastic agents (i.e. hyaluronic acid, chondroitin sulfate, hydroxypropyl methylcellulose) can consist of proteins, peptides, nucleoproteins, nucleic acids, endotoxins, and pyrogens. However, it is possible that viscoelastic agents which by present analytical techniques appears to be free of these impurities will cause cellular reactions when implanted at undiluted therapeutic concentrations. In is uncertain, if these impurities activate compliment via the classic or non-classical compliment pathways.

The present invention specifically relates to a non-primate process that consists of the surgical replacement of a small volume of the central gel vitreous of the rabbit with a viscoelastic agent or solution and measuring the invasion of white blood cells into the vitreous and anterior chamber at 48 hours post injection. Additional parameters measured are anterior chamber flare, haze and flare in the vitreal chamber, ocular fundus clarity, presence of iris congestion, lens involvement, corneal clarity, conjunctival congestion and conjunctival swelling. In this vitreal replacement process, the rabbit is evaluated prior to injection of the viscoelastic agent or solution and 48 hours post injection. Each parameter is evaluated on a scale of 0 to 5. A non-inflammatory sample consists of a mean total score equal to or less than one or a vitreal cell count less than 50 cells/mm$^3$. This is an extremely sensitive quantitative system for detecting small amounts of inflammatory agents in viscoelastic agents or solutions. This invention pertains to the use of this non-primate vitreal replacement process to distinguish between inflammatory and non-inflammatory viscoelastic agents and solutions for use in veterinary and human applications.

One significant feature of the present invention is that the vitreal replacement process utilizes a non-primate for the screening of viscoelastics for veterinary or human use.

Another specific aspect of the present invention relates to a non-primate process that consists of the surgical replacement of a small volume of the central gel vitreous of the rabbit with a viscoelastic agent or solution and measuring the invasion of white blood cells into the vitreous and anterior chamber at 48 hours post injection.

Still, another specific feature of this invention is that the inflammatory response to viscoelastic agents or solutions can be quantified as defined by the following parameters: anterior chamber flare, haze and flare in the vitreal chamber, ocular fundus clarity, presence of iris congestion, lens involvement, corneal clarity, conjunctival congestion and conjunctival swelling in the non-primate process. In this vitreal replacement process, the animal is evaluated prior to injection of the viscoelastic agent or solution and 48 hours post injection.

Having thus described the embodiments of the present invention, it is a principal object hereof to provide a non-primate vitreal replacement process that quantitates the inflammatory response to and subsequent suitability of viscoelastic agents or solutions for use in all surgical and non-surgical applications including, but not limited to ophthalmology, orthopeadics, dermatology, gastroenterology, gynecology, nephrology, neurology, obstetrics, onocology, otolaryngology, pediatrics, pharmacology, rheumatology, urology.

Thus, one principle object of this present invention is to quantitatively distinguish between inflammatory and non-inflammatory viscoelastic agents or solutions utilizing a non-primate vitreal replacement process.

Various modifications can be made to the present invention without departing from the apparent scope of the present invention. Other non-primate animals such as a cat may be suitable in lieu of the rabbits and are within the teachings of the present invention.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein:

FIGS. 1A, 1B, and 1C are Table I;
FIGS. 2A, 2B, and 2C are Table II;
FIG. 3 is Table III; and
FIG. 4 is Table IV.

DESCRIPTION OF THE PREFERRED EMBODIMENTS

The process by which a non-primate vitreal replacement process quantitates the inflammatory response to viscoelastic agents or solutions. More specifically, the rabbit vitreal replacement process of the present invention consists of the surgical replacement of a small volume of the central gel vitreous of the rabbit with a viscoelastic agent or solution and measuring the invasion of white blood cells in the vitreous and anterior chamber at 48 hours post injection. Additional parameters measured are anterior chamber flare, haze and flare in the vitreal chamber, ocular fundus clarity, presence of iris congestion, lens involvement, corneal clarity, conjunctival congestion and conjunctival swelling. In this process, the rabbit is evaluated prior to injection of the viscoelastic agent or solution and 48 hours post injection. Each parameter is evaluated on a scale of 0 to 5. A non-inflammatory sample consists of a mean total score of equal to or less than one or a vitreal cell count less than 50 cells/mm$^3$. This is an extremely sensitive system for detecting small amounts of inflammatory agents in viscoelastic agents or solutions. The test solution is rated as acceptable for veterinary or human use if a non-inflammatory response is obtained in this process.

VITREAL REPLACEMENT TEST IN THE NEW ZEALAND WHITE RABBIT

The New Zealand White rabbit is used to determine the inflammatory nature of the viscoelastic agent or solution. The rabbit has a gel-like central vitreous humor, in contrast to the liquid vitreous of the owl monkey. The owl monkey is a nocturnal, primate and has unusually large vitreal chamber, with the highest hyaluronic acid concentration in the vitreous of all known primate eyes including humans. (Osterlin, S. E. (1968) The synthesis of hyaluronic acid in the vitreous III. In vivo metabolism in owl monkeys. Exp. Eye. Res. 7,524-33.) Additionally the vitreal chamber of the owl monkey has the lowest protein content of all known connective tissue compartments (Balazs, E. A. and Sundblad, L. (1959). Viscosity of hyaluronic acid solutions containing proteins. Acta. Soc. Med. Upsaliensis 64,137-146). After repeated injections (7-9) of Healon ®, leucocyte counts were considered non-inflammatory. (Denlinger, J. L. and Balazs, E. A., Replacement of the Liquid Vitreous with Sodium Hyaluronate in Monkeys. Experimental Eye Research (1980) 31, 81-99). This data supports that the owl monkey is unique in its vitreal chamber characteristics as it relates to hyaluronic acid concentration, protein concentration, liquid vitreous center and inflammatory response, with regards to other primates, including humans. It is suggested that the owl monkey may illicit a reduced inflammatory response, based on these inherent differences. It is therefore, the main objective of this invention to utilize a unique non-primate process to determine the inflammatory response of viscoelastic agents and solutions for use in veterinary and human applications.

New Zealand White adult rabbits (5-6 lbs) are used for this vitreal replacement study. Animals with pre-existing ocular abnormalities are excluded from this test. General anesthesia is achieved by intramuscular injection of Rompin (10 mg/kg) and Ketamine HCl (50 mg/kg) of body weight. The eyes are dilated with topical ophthalmic phenylephrine HCl and 1% cyclopentolate HCl. After the eye is fully dialated, it is examined with a slit lamp. The cornea, anterior chamber, lens and iris are evaluated first. The anterior chamber must be free of cells and flare, with no iris congestion, lens opacities nor conjunctival congestion, swelling or discharge. Any abnormalities in the cornea, iris, or lens should be noted. Under an operating microscope, the vitreous should be evaluated for flare, cells, haze, and keratic precipitates. The clarity of the ocular fundus is also evaluated. Each of these parameters are evaluated on a clinical 1-5 scale (see Table I). If any ocular abnormalities are noted in the anterior or posterior chambers of the eye the rabbit is not used.

One drop of proparacaine 0.5% (Alcon Laboratories, Inc., Fort Worth, Tex.) is administered topically prior to intravitreal injection. All injected viscoelastic solutions should be sterile and administered undiluted.

Under a surgical microscope the conjunctival sac is flushed with sterile BSS and a 6-0 silk suture is placed beneath the superior extraocular muscle and clamped with a hemostat to retract the eye to reduce ocular movement. Under sterile conditions, a four to five millimeter incision is made through the conjunctiva and Tenon's capsule about 3 mm to 5 mm from the limbus to expose the sclera in a region of the parsplana just lateral to the superior rectus muscle. A 8-0 coated vicryl purse string type suture is then placed in the sclera in a circular fashion and left untied. A 19 gauge needle on a three cc syringe is then passed through the sclera in the area enclosed by the purse-string suture into the center of the vitreous humor. A small volume of vitreous (0.4 cc to 0.5 cc) is then withdrawn as atraumatically as possible. This volume of vitreous is then replaced with an equal volume (0.4 cc to 0.5 cc) of test viscoelastic material. In the control eye, vitreous humor is removed, and is not replaced with a viscoelastic material. A 25 gauge needle is then inserted through the same puncture hole, and the test or positive control material is instilled into the center of the vitreous body. The needle is then withdrawn and the wound closed by tightening the purse-string suture. The withdrawal and injection should be done slowly. The 6-0 silk suture is removed and the eye is returned to the normal position and antibiotic ointment is applied topically. The eye is then examined, to check for possible hemorrhage in the vitreous. If the eye has a hemorrhage, this eye cannot be used for evaluation of the viscoelastic material. Evaluation of inflammatory response (FIG. 2) is also made immediately after the injection of the viscoelastic or test material.

Observation of the rabbit takes place 48 hours after injection of the viscoelastic material. General anesthesia is achieved by intramuscular injection of Rompin (10 mg/kg) and Ketamine HCl (50 mg/kg) of body weight. The eyes are dilated with topical ophthalmic phenylephrine HCl and 1% cyclopentolate HCl. After the eye is fully dialated, it is examined with a slit lamp. The cornea, anterior chamber, lens and iris are evaluated first. The anterior chamber is graded for cells and flare, iris congestion, lens opacities, conjunctival congestion, swelling and discharge. Any abnormalities in the cornea, iris, or lens should be noted. Under an operating microscope, the vitreous should be evaluated for flare, cells, haze, and keratic precipitates. The clarity of the ocular fundus is also evaluated. Each of these parameters are evaluated on a clinical 1-5 scale (see FIG. 2).

At 48 hours post-injection, under sterile conditions, approximately 0.2 cc aqueous is removed by passing a 27 gauge needle, with a 1 cc syringe attached, anterior to the limbus into the anterior chamber. Care should be taken not to come in contact with the corneal endothelium, iris or lens. Cell content of the small aqueous sample is counted. The sample is transferred to a blood counting chamber and a count of white blood cells performed. The appropriate conversion factors are utilized and the results are recorded as cells per cubic mm aqueous humor.

A small volume (0.4 cc to 0.5 cc) of vitreous is removed by tapping the vitreous with a 19 gauge needle 90° from the original injection site. Cell content of the small vitreous sample is counted. The sample is transferred to a blood counting chamber and a count of white blood cells performed. The appropriate conversion factors are utilized and the results are recorded as cells per cubic mm aqueous humor or vitreous. The cytological examination of the vitreous and the aqueous humor at various times after the injection of the viscoelastic material is most important for the quantitative evaluation of a possible acute or chronic inflammatory reaction.

The viscoelastic is acceptable for veterinary or human use if the 48-hour postoperative evaluation of the rabbit eye meets the following criteria (see FIG. 3): A non-inflammatory sample has a mean clinical score equal to or less than one or a vitreal cell count less than 50 cells/mm$^3$.

EXAMPLE ONE

Comparison of the Rhesus Vitreal Replacement Process and the New Zealand White Rabbit Process In this study, four adult female rhesus monkeys (Macaca mulatta) were used in this study. These monkeys weighed from 6-8 kg. Four adult female New Zealand White rabbits (2.5-3.0 kg) were also used in this study. In each animal process, the vitreous was removed and replaced with Ocugel TM (Surgidev Corporation, Goleta, CA), a commercially available viscoelastic as described previously. Animals were evaluated prior to and 48 hours post-injection as defined by the parameters listed previously. The results are shown in FIG. 4. In both the primate and rabbit process the Ocugel TM sample was found to be non-inflammatory. In the rabbit process, a greater inflammatory response was observed with respect to aqueous flare, vitreal chamber cells, conjunctival congestion, conjunctival congestion and iris congestion. The inflammatory response was more easily observed in the non-pigmented rabbit eye as compared to the pigmented primate eye.

EXAMPLE TWO

The Inflammatory Response in the Rabbit Vitreal Replacement Process

In this study, twenty-four adult female New Zealand White rabbits (2.5-3.0 kg) were used. In the test eyes the vitreous was removed and replaced with Ocugel TM (Surgidev Corporation, Inc. Goleta, CA), a commercially available viscoelastic as described previously. In the positive control group, the vitreous was removed and replaced with Zymozan A, (Sigma Chemical Company, St. Louis, MO) at a final concentration of 1 mg/ml in sterile BSS (Alcon, Fort Worth, TX). Animals were evaluated prior to and 48 hours post-injection as defined by the parameters listed previously. Cell counts and ocular inflammatory response are determined to evaluate the inflammatory response to the injected materials. The results are shown in FIG. 4.

Zymozan A, a known complement activator demonstrated an inflammatory response after injection into the vitreal chamber of the rabbit. The zymozan A positive control test group demonstrated elevated inflammatory responses with respect to aqueous flare, anterior chamber cells, vitreal chamber cells, vitreal haze, ocular fundus, conjunctival congestion, conjunctival swelling, conjunctival discharge, iris congestion, and corneal clarity. The test material Ocugel TM was found to be non-inflammatory in this vitreal replacement process.

We claim:

1. Vitreal replacement process comprising the steps of:
   a. procure an animal and grade the animal's eye by a grading of an inflammatory response scale;
   b. place a suture means in the sclera, extract by a syringe and needle a vitreal humor from the posterior chamber of the animal's eye;
   c. count the number of inflammatory cells in the vitreal humor sample, whereby the eye is graded for inflammatory response;
   d. put in an approximate amount of like solution;
   e. close the suture means;
   f. evaluate the eye for vitreal hemorrhage;
   g. wait 48 hours;

h. grade the eye by the grading scale;
i. tap the anterior chamber of the eye, and remove an aqueous sample;
j. tap the posterior chamber of the eye, and remove a vitreal humor sample;
k. count the number of inflammatory cells in the aqueous and vitreous samples whereby the eye is graded for the inflammatory response by the grading of the inflammatory response and,
l. compare to a non-inflammatory response in an animal.

2. The said process of claim 1 where said waiting time is 24 to 96 hours.

3. The said process of claim 1 where said animal is a non-primate.

4. The said process of claim 3 where said waiting time is 24 to 96 hours.

5. The said process of claim 1 where said animal is a rabbit.

6. The said process of claim 5 where said waiting time is 24 to 96 hours.

7. Vitreal replacement process comprising the steps of:
a. procure an animal and grade the animal's eye by a grading of an inflammatory response scale;
b. place a suture means in the sclera, extract by a syringe and needle a vitreal humor from the posterior chamber of the animal's eye;
c. count the number of inflammatory cells in the vitreal humor sample, whereby the eye is graded for inflammatory response;
d. put in an approximate amount of like solution;
e. close the suture means;
f. evaluate the eye for vitreal hemorrhage;
g. wait 48 hours;
h. grade the eye by the grading scale;
i. tap the anterior chamber of the eye, and remove an aqueous sample;
j. tap the posterior chamber of the eye, and remove a vitreal humor sample; and,
k. count the number of inflammatory cells in the aqueous and vitreous samples whereby the eye is graded for a inflammatory response.

8. the said process of claim 7 where said waiting time is 24 to 96 hours.

9. The said process of claim 7 where said animal is a non-primate.

10. The said process of claim 9 where said waiting time is 24 to 96 hours.

11. The said process of claim 7 where said animal is a rabbit.

12. The said process of claim 11 where said waiting time is 24 to 96 hours.

13. Vitreal replacement process comprising the steps of:
a. procure an animal and grade the animal's eye by a grading of an inflammatory response scale;
b. place a suture means in the sclera, extract by a syringe and needle vitreal humor from the posterior chamber of the animal's eye;
c. count the number of inflammatory cells in the vitreal humor sample, whereby the eye is graded for inflammatory response;
d. put in an approximate amount of like solution;
e. close the suture means;
f. evaluate the eye for vitreal hemorrhage;
g. wait 48 hours;
h. grade the eye by the grading scale;
i. tap the posterior chamber of the eye, and remove a vitreal humor sample;
j. count the number of inflammatory cells in the vitreous sample whereby the eye is graded for the inflammatory response; and,
k. compare to a non-inflammatory response in an animal.

14. The said process of claim 13 where said waiting time is 24 to 96 hours.

15. The said process of claim 13 where said animal is a non-primate.

16. The said process of claim 15 where said waiting time is 24 to 96 hours.

17. The said process of claim 13 where said animal is a rabbit.

18. The said process of claim 17 where said waiting time is 24 to 96 hours.

19. Vitreal replacement process comprising the steps of:
a. procure an animal and grade the animal's eye by a grading of an inflammatory response scale;
b. place a suture means in the sclera, extract by a syringe and needle vitreal humor from the posterior chamber of the animal's eye;
c. count the number of inflammatory cells in the vitreal humor sample, whereby the eye is graded for inflammatory response;
d. put in an approximate amount of like solution;
e. close the suture means;
f. evaluate the eye for vitreal hemorrhage;
g. wait 48 hours;
h. grade the eye by the grading scale;
i. tap the posterior chamber of the eye, and remove a vitreal humor sample; and,
j. count the number of inflammatory cells in the vitreous sample whereby the eye is graded for the inflammatory response.

20. The said process of claim 19 where said waiting time is 24 to 96 hours.

21. The said process of claim 19 where said animal is a non-primate.

22. The said process of claim 21 where said waiting time is 24 to 96 hours.

23. The said process of claim 19 where said animal is a rabbit.

24. The said process of claim 23 where said waiting time is 24 to 96 hours.

* * * * *